US012678427B2

(12) United States Patent
Stankovic-Valentin et al.

(10) Patent No.: US 12,678,427 B2
(45) **Date of Patent: *Jul. 14, 2026**

(54) COMBINATION THERAPY HAVING ANTIOXYDANT PROPERTIES

(71) Applicant: GENFIT, Loos (FR)

(72) Inventors: Nicolas Stankovic-Valentin, Mouscron (BE); Peggy Parroche, Loos (FR); Corinne Foucart, La Madeleine (FR); Robert Walczak, Lille (FR)

(73) Assignee: GENFIT, Loos (FR)

( * ) Notice: Subject to any disclaimer, the term of this patent is extended or adjusted under 35 U.S.C. 154(b) by 1088 days.

This patent is subject to a terminal disclaimer.

(21) Appl. No.: 17/772,158

(22) PCT Filed: Oct. 27, 2020

(86) PCT No.: PCT/EP2020/080205
§ 371 (c)(1),
(2) Date: Apr. 27, 2022

(87) PCT Pub. No.: WO2021/083912
PCT Pub. Date: May 6, 2021

(65) Prior Publication Data

US 2022/0401420 A1 Dec. 22, 2022

(30) Foreign Application Priority Data

Oct. 28, 2019 (EP) .................................... 19205763

(51) Int. Cl.

| | |
|---|---|
| ***A61K 31/426*** | (2006.01) |
| ***A61K 31/192*** | (2006.01) |
| ***A61P 1/16*** | (2006.01) |

(52) U.S. Cl.
CPC .......... *A61K 31/426* (2013.01); *A61K 31/192* (2013.01); *A61P 1/16* (2018.01)

(58) Field of Classification Search
CPC ........ A61K 31/426; A61K 31/192; A61P 1/16
See application file for complete search history.

(56) References Cited

U.S. PATENT DOCUMENTS

| | | | | |
|---|---|---|---|---|
| 11,033,534 | B2 * | 6/2021 | Foucart | A61P 9/10 |
| 12,053,456 | B2 * | 8/2024 | Foucart | A61P 1/00 |
| 12,208,087 | B2 * | 1/2025 | Parroche | A61K 45/06 |

FOREIGN PATENT DOCUMENTS

| | | |
|---|---|---|
| WO | WO 2018/138352 | 8/2018 |
| WO | WO 2019/053233 | 3/2019 |
| WO | WO 2019/053235 | 3/2019 |

OTHER PUBLICATIONS

Walczak, R. et al. "Elafibranor and nitazoxanide synergize to reduce fibrosis in a NASH model" Poster Presentation THU-494, *Journal of Hepatology*, Mar. 28, 2018, pp. S352-S353, vol. 68.
Written Opinion in International Application No. PCT/EP2020/080205, Jan. 20, 2021, pp. 1-9.

* cited by examiner

*Primary Examiner* — Kevin E Weddington
(74) *Attorney, Agent, or Firm* — SALIANCHIK, LLOYD & EISENSCHENK

(57) ABSTRACT

The present invention relates to novel uses of nitazoxanide, or analogues thereof.

8 Claims, 3 Drawing Sheets

COMBINATION THERAPY HAVING ANTIOXYDANT PROPERTIES

CROSS-REFERENCE TO RELATED APPLICATION

This application is the U.S. national stage application of International Patent Application No. PCT/EP2020/080205, filed Oct. 27, 2020.

TECHNICAL FIELD

The present invention relates to a combination product providing antioxidant effects.

BACKGROUND

Elafibranor (ELA; 1-[4-methylthiophenyl]-3-[3,5-dimethyl-4-carboxydimethylmethyloxyphenyl]prop-2-en-1-one) is a compound having advantageous properties for the treatment of a number of gastroenterology and liver diseases. It is currently evaluated in a clinical phase 3 study for the treatment of non-alcoholic steatohepatitis (NASH) and in a clinical phase 2 for the treatment of primary biliary cholangitis (PBC).

Nitazoxanide (NTZ; [2-[(5-nitro-1,3-thiazol-2-yl)carbamoyl]phenyl]ethanoate is a medicament authorized in the United States for the treatment of diarrhea caused by the protozoan parasites *Cryptosporidium parvum* and Giardia intestinalis. Several studies have also shown that NTZ has antiviral and antitumoral properties. NTZ was also recently shown by the present Applicant to have antifibrotic properties (WO2017178172) and is currently evaluated for its safety and efficacy on a population with NASH-induced stage 2 or 3 fibrosis.

SUMMARY OF THE INVENTION

The inventors herein show that a combination of elafibranor with NTZ has antioxidant properties, which is higher than the antioxidant properties obtained with each compound used alone. In particular, this observation is made on relevant oxidative markers such as 4-hydroxynonenal (4-HNE). This finding opens new therapeutic opportunities.

In particular, the inventors found that elafibranor combined with NTZ activates a wide range of genes involved at different stages of the defense system against oxidative stress. In particular the inventors have shown that NTZ combined with elafibranor activates the expression of genes involved in the first line of defense against oxidative stress, but also the expression of different glutathione S-transferase (GST) genes that are involved in later steps of antioxidant mechanism. Indeed, GST are a family of enzymes that play an important role in detoxification by catalysing the conjugation of many hydrophobic and electrophilic compounds with reduced glutathione such as products of peroxidation. Their activation can thus advantageously be implemented for protecting cells, tissues and organs against oxidative stress.

Moreover, the inventors have shown that Tizoxanide (TZ), the active metabolite of NTZ, combined to ELA was able to induce the Nrf2-antioxidant pathway which plays an important role in cellular antioxidant defence. Unexpectedly, this induction of Nrf2-ARE-mediated transcription with the TZ/ELA combination was significantly higher compared to those obtained with each agent alone reflecting the beneficial therapeutic effect obtained with the combined products.

DETAILED DESCRIPTION OF THE INVENTION

Herein is disclosed a combination product comprising:

(i) elafibranor, a metabolite of elafibranor, a pharmaceutically acceptable salt of elafibranor, or a pharmaceutically acceptable salt of a metabolite of elafibranor, and (ii) a compound of formula (I) as defined below, or a pharmaceutical salt thereof.

As shown by the inventors, this combination product can be used as an antioxidant.

In the context of the present application, "component (i)" refers to "elafibranor, a metabolite of elafibranor, a pharmaceutically acceptable salt of elafibranor, or a pharmaceutically acceptable salt of a metabolite of elafibranor", or to particular embodiments thereof as disclosed below.

In the context of the present application, "component (ii)" refers to a compound of formula (I), or to particular embodiments thereof as disclosed below.

Formula (I) defines a family of compounds including NTZ and derivatives thereof. In particular, formula (I) defines a family of prodrugs of TZ, the active metabolite of NTZ.

In a particular embodiment, the combination product of the invention is for use for its hepatic antioxidant properties.

In a further particular embodiment, the combination product of the invention is for use in a method for the treatment of a disease in which oxidative stress is involved. Diseases in which oxidative stress is involved are commonly known to those skilled in the art who can refer, among many other sources to de Araujo et al. (de Araújo, Martins et al. 2016).

For example, subjects who can benefit from the invention include, without limitation, those suffering from neurological disorders such as central nervous system disorders, metabolic conditions, cardiovascular diseases, cataract, atherosclerosis, ischemia such as myocardial ischemia, ischemic brain damage, lung ischemia-reperfusion injury, scleroderma and stroke, inflammation such as inflammatory bowel disease, rheumatoid arthritis, respiratory diseases, autoimmune diseases, kidney diseases and skin conditions.

The term "treatment" or "treating" refers to the curative or preventive treatment of a disease in a subject in need thereof. The treatment involves the administration of the compound of the invention to a subject having a declared disease, to prevent, cure, delay, reverse, or slow down the progression of the disease, improving thereby the condition of the subject. The compound of the invention can also be administered to a subject who is healthy or at risk of developing a disease. The subject to be treated is a mammal, preferably a human. The subject to be treated according to the invention can be selected on the basis of several criteria associated to the specific disease the treatment of which is sought such as previous drug treatments, associated pathologies, genotype, exposure to risk factors, viral infection, as well as on the basis of the detection of any biomarker relevant to the disease.

In addition, the invention relates to the combination product disclosed herein, for use in a method for treating the oxidative stress associated to a disease, in particular a disease selected in the group consisting of neurological disorders such as central nervous system disorders, metabolic conditions, cardiovascular diseases, cataract, atherosclerosis, ischemia such as myocardial ischemia, ischemic brain damage, lung ischemia-reperfusion injury, scleroderma and stroke, inflammation such as inflammatory bowel disease, rheumatoid arthritis, respiratory diseases, autoimmune diseases, liver diseases, kidney diseases, skin conditions, infections and cancers.

Neurological disorders include, without limitation, Alzheimer's disease, Parkinson's disease, Huntington's disease, tardive dyskinesia, epilepsy and acute diseases of the central nervous system such as spinal cord injuries and/or brain trauma.

Metabolic conditions include, without limitation, obesity, insulin resistance, dyslipidemia, impaired glucose tolerance, high blood pressure, atherosclerosis and diabetes, such as type 1 or type 2 diabetes. Metabolic conditions also include the metabolic syndrome.

In a particular embodiment, the combination product disclosed herein is used in a method for treating infection-induced oxidative stress, such as virus-induced oxidative stress, in particular human immunodeficiency virus-induced oxidative stress, influenza virus-induced oxidative stress, hepatitis B virus-induced oxidative stress, hepatitis C virus-induced oxidative stress, encephalomyocarditis virus-induced oxidative stress, respiratory syncytial virus-induced oxidative stress and dengue virus-induced oxidative stress.

The invention further relates to the combination product disclosed, for use in a method for treating the oxidative stress associated to a liver disorder. In particular, the subject to be treated can have non-alcoholic fatty liver disease (NAFLD), NAFLD with liver fibrosis, NASH, NASH with liver fibrosis, or NASH-related cirrhosis. The invention therefore also relates to the combination product as defined herein, for use in a method for treating the oxidative stress associated to NAFLD, the oxidative stress associated to NAFLD with liver fibrosis, the oxidative stress associated to NASH, the oxidative stress associated to NASH with liver fibrosis, or the oxidative stress associated to NASH-related cirrhosis.

In addition, the invention relates to a method for the treatment of oxidative stress, comprising administering to a subject in need thereof a therapeutically effective amount of:

(i) elafibranor, a metabolite of elafibranor, a pharmaceutically acceptable salt of elafibranor, or a pharmaceutically acceptable salt of a metabolite of elafibranor, and (ii) a compound of formula (I) or a pharmaceutically acceptable salt thereof Furthermore, the invention relates to a method for the treatment a disease in which oxidative stress is involved, comprising administering to a subject in need thereof a therapeutically effective amount of:

(i) elafibranor, a metabolite of elafibranor, a pharmaceutically acceptable salt of elafibranor, or a pharmaceutically acceptable salt of a metabolite of elafibranor, and (ii) a compound of formula (I) or a pharmaceutically acceptable salt thereof.

The invention further relates to a method for treating the oxidative stress associated to a disease, comprising administering to a subject in need thereof a therapeutically effective amount of:

(i) elafibranor, a metabolite of elafibranor, a pharmaceutically acceptable salt of elafibranor, or a pharmaceutically acceptable salt of a metabolite of elafibranor, and (ii) a compound of formula (I) or a pharmaceutically acceptable salt thereof.

In a particular embodiment, the oxidative stress is associated to a disease selected in the group consisting of neurological disorders such as central nervous system disorders, metabolic conditions, cardiovascular diseases, cataract, atherosclerosis, ischemia such as myocardial ischemia, ischemic brain damage, lung ischemia-reperfusion injury, scleroderma and stroke, inflammation such as inflammatory bowel disease, rheumatoid arthritis, respiratory diseases, autoimmune diseases, liver diseases, kidney diseases, skin conditions, infections and cancers, as defined above.

In addition the invention relates to a method for the treatment of infection-induced oxidative stress, such as virus-induced oxidative stress, in particular human immunodeficiency virus-induced oxidative stress, influenza virus-induced oxidative stress, hepatitis B virus-induced oxidative stress, hepatitis C virus-induced oxidative stress, encephalomyocarditis virus-induced oxidative stress, respiratory syncytial virus-induced oxidative stress and dengue virus-induced oxidative stress, wherein said method comprises administering to a subject in need thereof a therapeutically effective amount of:

(i) elafibranor, a metabolite of elafibranor, a pharmaceutically acceptable salt of elafibranor, or a pharmaceutically acceptable salt of a metabolite of elafibranor, and (ii) a compound of formula (I) or a pharmaceutically acceptable salt thereof.

The invention further relates to a method for the treatment of oxidative stress associated to a liver disorder, comprising administering to a subject in need thereof a therapeutically effective amount of:

(i) elafibranor, a metabolite of elafibranor, a pharmaceutically acceptable salt of elafibranor, or a pharmaceutically acceptable salt of a metabolite of elafibranor, and (ii) a compound of formula (I) or a pharmaceutically acceptable salt thereof.

In a particular embodiment, the oxidative stress which is treated is associated to NAFLD, NAFLD with liver fibrosis, NASH, NASH with liver fibrosis or NASH-related-cirrhosis.

According to the present invention, a compound of formula (I) is defined as follows:

(I)

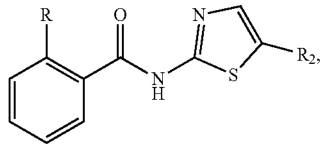

in which

R represents a O—R1 group or an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, or a moiety of formula (A):

(A)

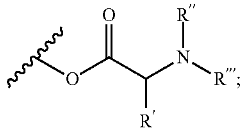

wherein R' represents an (C1-C6)alkyl group, an (C2-C6) alkenyl group, an (C2-C6)alkynyl group, a (C3-C14) cycloalkyl group, (C3-C14)cycloalkyl(C1-C6)alkyl group, a (C3-C14)cycloalkyl(C1-C6)alkenyl group, a (C3-C14)cycloalkenyl group, a (C3-C14)cycloalkenyl (C1-C6)alkyl group, a (C3-C14)cycloalkenyl(C2-C6) alkenyl group, a (C3-C14)cycloalkenyl(C2-C6)alkynyl group; R" and R'", independently, represent a hydrogen atom, an (C1-C6)alkyl group, or a nitrogen protecting group or a pharmaceutically acceptable salt thereof;

R1 represents a hydrogen atom or a (C1-C6)alkylcarbonyl group; and

R2 represents a halogen, preferably a chlorine atom, or a NO2 group.

In a particular embodiment, the compound of formula (I) is selected from:

NTZ or a pharmaceutically acceptable salt thereof:

(I-a)

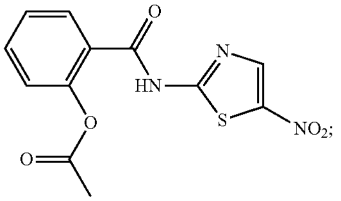

TZ or a pharmaceutically acceptable salt thereof:

(I-b)

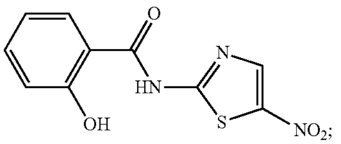

tizoxanide glucuronide (TZG) or a pharmaceutically acceptable salt thereof:

(I-c)

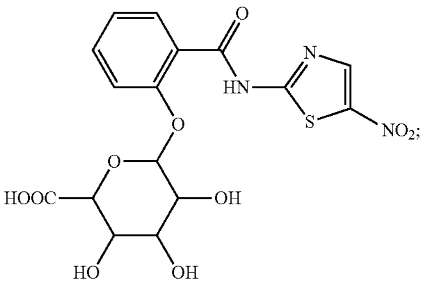

2-[(5-chloro-1,3-thiazol-2-yl)carbamoyl]phenyl]ethanoate (RM5038) or a pharmaceutically acceptable salt thereof.

(I-d)

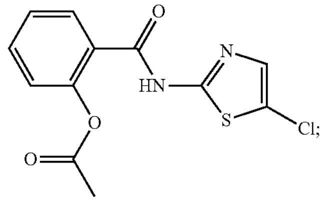

N-(5-chlorothiazol-2-yl)-2-hydroxybenzamide (RM4848) or a pharmaceutically acceptable salt thereof:

(I-e)

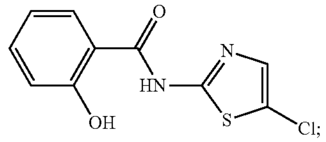

RM4848-glucuronide or a pharmaceutically acceptable salt thereof:

(I-f)

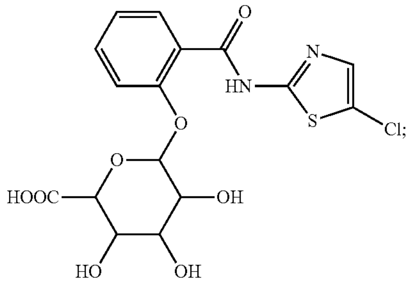

[2-[(5-nitrothiazol-2-yl)carbamoyl]phenyl]-2-amino-3,3-dimethylbutanoate, in particular (S)-[2-[(5-nitrothiazol-2-yl)carbamoyl]phenyl]-2-amino-3,3-dimethylbutanoate of formula (I-g), or a pharmaceutically acceptable salt thereof such as its hydrochloride salt (RM5061) of formula (I-h):

(I-g)

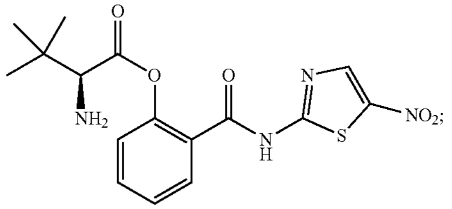

(I-h)

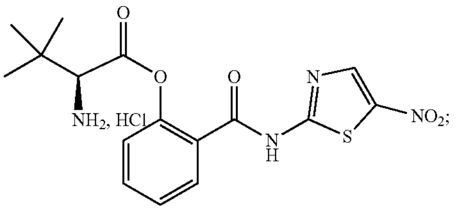

[2-[(5-nitrothiazol-2-yl)carbamoyl]phenyl]-2-amino-3-methylpentanoate, in particular (2S,3S)-[2-[(5-nitrothiazol-2-yl)carbamoyl]phenyl]-2-amino-3-methylpentanoate of formula (I-i), or a pharmaceutically acceptable salt thereof such as its hydrochloride salt (RM5066) of formula:

(I-i)

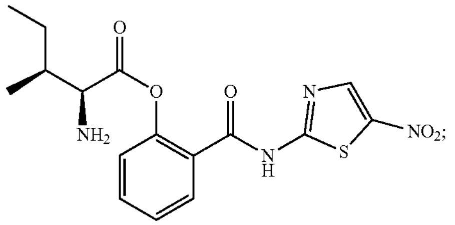

[2-[(5-chlorothiazol-2-yl)carbamoyl]phenyl]-2-amino-3,3-dimethylbutanoate, in particular (S)-[2-[(5-chlorothiazol-2-yl)carbamoyl]phenyl]-2-amino-3,3-dimethylbutanoate of formula (I-j), or a pharmaceutically acceptable salt thereof such as its hydrochloride salt (RM5064) of formula (I-k):

(I-j)

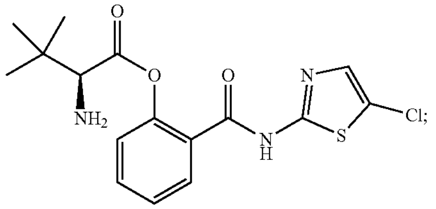

(I-k)

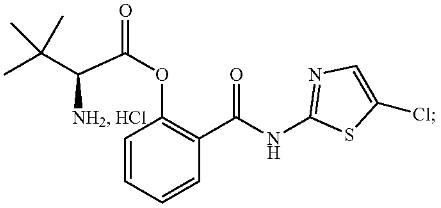

[2-[(5-chlorothiazol-2-yl)carbamoyl]phenyl]-2-amino-3-methylpentanoate, in particular (2S,3S)-[2-[(5-chlorothiazol-2-yl)carbamoyl]phenyl]-2-amino-3-methylpentanoate of formula (I-l), or a pharmaceutically acceptable salt thereof such as its hydrochloride salt (RM5065) of formula (I-m):

(I-j)

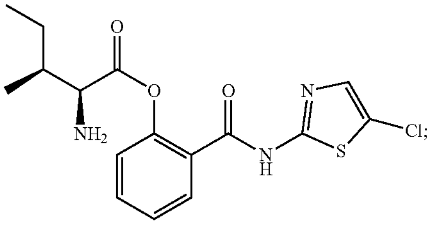

and

-continued (I-k)

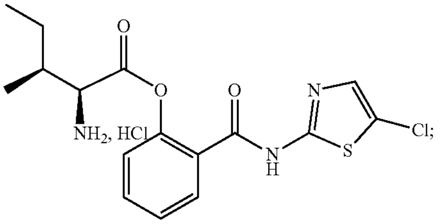

In a particular embodiment, the compound of formula (I) is selected from NTZ, TZ, a pharmaceutically acceptable salt of NTZ and a pharmaceutically acceptable salt of TZ.

In a further particular embodiment, the compound of formula (I) is selected from NTZ and TZ.

In yet a further particular embodiment, the compound of formula (I) is NTZ or a pharmaceutically acceptable salt thereof. In another embodiment, the compound of formula (I) is NTZ.

Elafibranor has the following Formula (II):

(II)

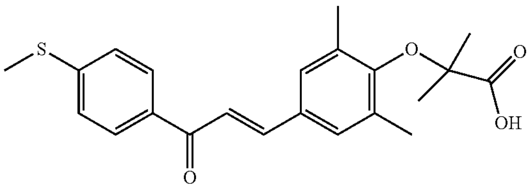

In a particular embodiment of the invention, a metabolite of elafibranor or a pharmaceutically acceptable salt of a metabolite of elafibranor is used. More particularly, the metabolite of elafibranor is 2-[2,6-dimethyl-4-[3-[4-(methylthio)phenyl]-3-oxo-propyl]phenoxy]-2-methylpropanoic acid.

In a further particular embodiment, elafibranor or a pharmaceutically acceptable salt thereof is used. In a more particular embodiment, elafibranor is used.

In a particular embodiment, the invention relates to the combination product as defined above for the treatment of the oxidative stress associated to a liver disorder, or to corresponding methods of treatment.

In a further particular embodiment, the invention relates to the treatment of the oxidative stress associated to liver fibrosis, comprising the administration of a therapeutically effective amount of (i) elafibranor, a metabolite thereof, a pharmaceutically acceptable salt of elafibranor, or a pharmaceutically acceptable salt of a metabolite of elafibranor; and (ii) NTZ, TZ, a pharmaceutically acceptable salt of NTZ or a pharmaceutically acceptable salt of TZ.

In a further particular embodiment, the invention relates to the treatment of the oxidative stress associated to NASH, comprising the administration of a therapeutically effective amount of (i) elafibranor, a metabolite thereof, a pharmaceutically acceptable salt of elafibranor, or a pharmaceutically acceptable salt of a metabolite of elafibranor; and (ii) NTZ, TZ, a pharmaceutically acceptable salt of NTZ or a pharmaceutically acceptable salt of TZ.

Synthesis of NTZ or analogues can be, for example, carried out as described by Rossignol et al. (Rossignol and Cavier 1975), or by any other way of synthesis known by a person skilled in the art.

Synthesis of elafibranor can be, for example, carried out as described for compound 29 in WO2004/005233.

The compounds disclosed herein can be included in one or several pharmaceutical compositions, which can further comprise a pharmaceutically acceptable carrier. A pharmaceutical composition can also comprise one or several excipients or vehicles, acceptable within a pharmaceutical context (e.g. saline solutions, physiological solutions, isotonic solutions, etc., compatible with pharmaceutical usage and well-known by one of ordinary skill in the art). A pharmaceutical composition can also comprise one or several agents or vehicles chosen among dispersants, solubilizers, stabilizers, preservatives, etc. Illustrative agents or vehicles useful for a liquid, injectable and/or solid pharmaceutical composition include, without limitation, methylcellulose, hydroxymethylcellulose, carboxymethylcellulose, polysorbate 80, mannitol, gelatin, lactose, vegetable oils, acacia and liposomes. The pharmaceutical composition can be for enteral or parenteral administration.

For example, the compound described herein can be formulated for oral, intravascular (e.g. intravenous or intra-arterial), intramuscular, intraperitoneal, subcutaneous, transdermal or nasal administration. The composition can be a solid or liquid dosage form. Illustrative formulations include, without limitation, injectable suspensions, suspensions for oral ingestion, gels, oils, ointments, pills, tablets, suppositories, powders, gel caps, capsules, aerosols, ointments, creams, patches or means of galenic forms or devices assuring a prolonged and/or slow release. For this kind of formulations, agents such as cellulose, carbonates or starches can be advantageously used.

As mentioned above, one or more compounds disclosed herein can be formulated as pharmaceutically acceptable salts, particularly acid or base salts compatible with pharmaceutical use. Salts can include pharmaceutically acceptable acid addition salts, pharmaceutically acceptable base addition salts, pharmaceutically acceptable metal salts, ammonium and alkylated ammonium salts. These salts can be obtained during the final purification step of a compound or by incorporating the salt into the previously purified compound.

According to a particular embodiment, the combination product of the invention is in the form of a pharmaceutical composition comprising both component (i) and component (ii) of the combination product as described above. Said pharmaceutical composition can further comprises one or more acceptable excipients. In a specific embodiment, the combination product of the invention is a pharmaceutical composition comprising:

(i) elafibranor, and (ii) NTZ or TZ, in particular NTZ.

In yet another specific embodiment, the combination product of the invention is a pharmaceutical composition comprising NTZ, TZ and elafibranor.

In another embodiment, the combination product of the invention is a kit of parts comprising component (i) and component (ii) as described above, for sequential, separate or simultaneous use. In this embodiment, each of the compounds can be formulated in different pharmaceutical compositions.

The frequency and/or dose relative to the administration can be adapted by one of ordinary skill in the art, in function of the subject to be treated, the pathology, the disease to be treated, the stage of the disease, the form of administration, etc. Typically, component (ii) of the combination product, in particular NTZ or a pharmaceutically acceptable salt thereof, can be administered at a dose comprised between 0.01 mg/day to 4000 mg/day, such as from 50 mg/day to 2000 mg/day, and particularly from 100 mg/day to 1000 mg/day, more particularly from 500 mg/day to 1000 mg/day.

Component (i) of the combination product, in particular elafibranor or a pharmaceutically acceptable salt thereof, can be administered at a dose comprised between 0.01 mg/day to 4000 mg/day, such as from 1 mg/day to 2000 mg/day, in particular from 25 to 1000 mg/day, more particularly from 50 to 200 mg/day, and even more particularly from 80 mg/day to 120 mg/day. In a particular embodiment, component (i) and component (ii) are orally administered at these doses, e.g. in the form of a pill or tablet. In a further particular embodiment, component (i) and component (ii) are in the same composition, such as an oral composition (e.g. a pill or a tablet) and are administered at these doses. In another embodiment, component (i) and component (ii) are in different compositions, such as different oral compositions (e.g. in different pills, in different tablets, or in a pill and in a tablet) and are administered at the above-mentioned doses. In another embodiment, component (i) and component (ii) are in different compositions, component (i) being in the form of a liquid suspension for oral ingestion and component (ii) being in the form of a tablet.

Administration can be performed daily or even several times per day, if necessary. The duration of the treatment will depend on the specific disease to be treated. For example, the administration can be performed during one or several days, such as during at least one day, at least two days, at least three days, at least four days, at least five days, at six two days or at least seven days. Alternatively, the administration can be performed for at least one week, at least two weeks, at least four weeks. For chronic diseases, administration can be considered for more than four weeks, such as for at least one month, two months, three months, four months, five months, six months or more than six months, such as for at least one year or several years. In some cases, the combination product of the invention can be administered during the lifetime of the subject.

In another preferred embodiment, the component (ii), preferably NTZ or a pharmaceutically acceptable salt thereof, is administered in the form of a pill or tablet intended for oral ingestion. In another particular embodiment, component (ii), preferably NTZ or a pharmaceutically acceptable salt thereof, is administered in the form of a suspension for an oral ingestion.

In another preferred embodiment, component (i), preferably elafibranor or a pharmaceutically acceptable salt thereof, is administered in the form of a pill or tablet intended for oral ingestion. In another particular embodiment, component (i), preferably elafibranor or a pharmaceutically acceptable salt thereof, is administered in the form of a suspension for an oral ingestion.

In a further aspect, the invention relates to a method for the treatment of a disease, comprising the administration of a composition of NTZ or a pharmaceutical salt thereof, wherein NTZ is administered at a dose comprised between 500 mg/day and 1000 mg/day, and elafibranor or a pharmaceutical salt thereof, wherein elafibranor is administered at a dose comprised between 80 mg/day and 120 mg/day wherein the disease is selected in the group consisting of Alzheimer's disease, Parkinson's disease, Huntington's disease, tardive dyskinesia, epilepsy, acute diseases of the central nervous system such as spinal cord injuries and/or brain trauma, obesity, insulin resistance, dyslipidemia, impaired glucose tolerance, high blood pressure, atherosclerosis and diabetes, such as type 1 or type 2 diabetes, metabolic syndrome, human immunodeficiency virus-induced oxidative stress, influenza virus-induced oxidative stress, HBV-induced oxidative stress, hepatitis C virus-induced oxidative stress, encephalomyocarditis virus-induced oxidative stress, respiratory syncytial virus-induced oxidative stress, dengue virus-induced oxidative stress, NAFLD-associated oxidative stress, NAFLD-associated oxidative stress with liver fibrosis, NASH-associated oxidative stress, NASH-associated oxidative stress with liver fibrosis, NASH-associated oxidative stress with liver cirrhosis, myocardial ischemia, ischemic brain damage, lung ischemia-reperfusion injury, scleroderma, stroke, inflammatory bowel disease and rheumatoid arthritis.

The invention is further described with reference to the following, non-limiting, examples.

EXAMPLES

Figure 1:
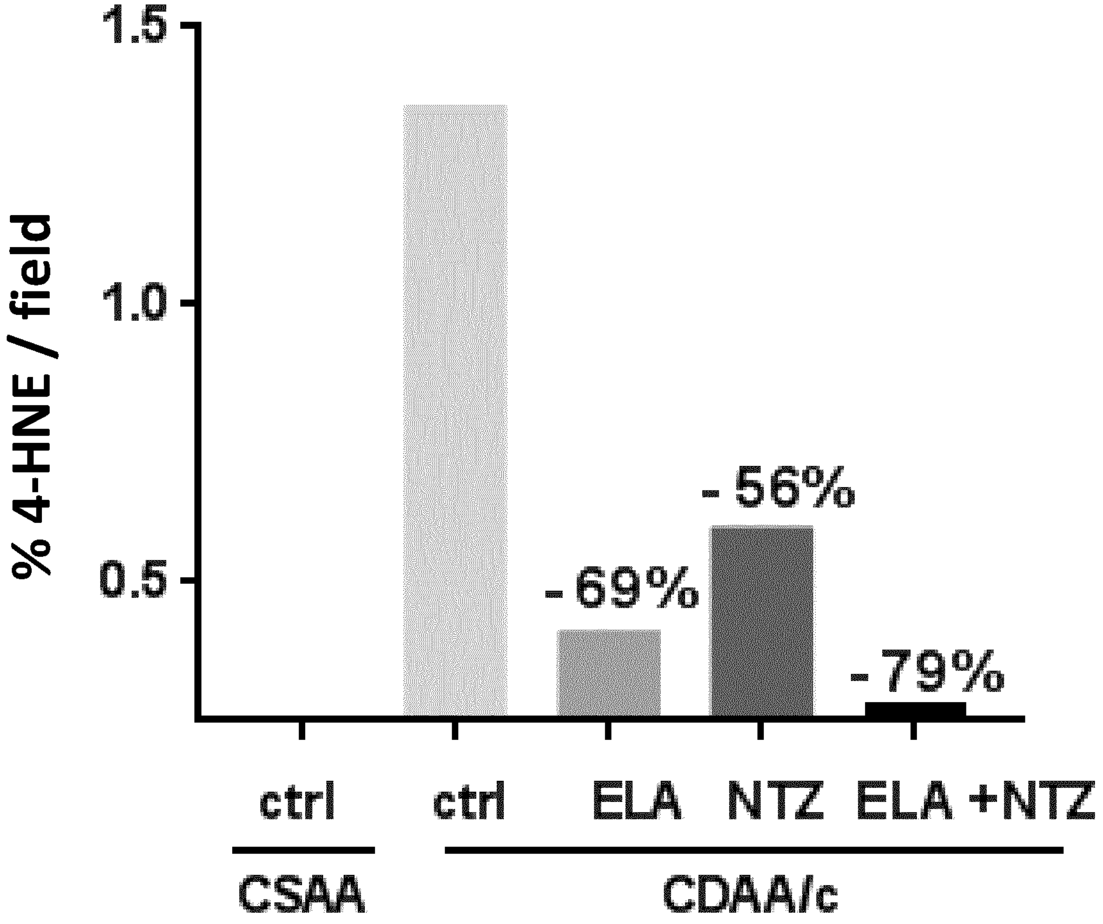
FIG. 1 is a graph representing the levels of 4-HNE as quantified by immunochemistry on liver samples from 6 week-old C57BL/6 mice fed a control (CSAA) diet, CDAA+1% CHOL (CDAA/c) diet, or CDAA/c diet supplemented with NTZ 100 mg/kg/day alone, ELA 1 mg/kg/day alone or combined NTZ 100 mg/kg/day/ELA 1 mg/kg/day for 12 weeks.

Evaluation of Elafibranor, Nitazoxanide and the Combination of Elafibranor+Nitazoxanide in a Chronic CDAA+1% Cholesterol Model of Fibrosing NASH (12 Weeks)

Material & Methods

Experimental Design

Given the prominent role of oxidative stress in NASH pathogenesis, we evaluated NTZ capacity to prevent redox homeostasis dysregulation in the CDAA/c diet induced NASH model.

The choline-deficient and L-amino acid-defined (CDAA) diet lacks choline, which is essential for hepatic β-oxidation and very low density lipoprotein production, and is believed to induce hepatocellular steatosis. Subsequently, lipid peroxidation and oxidative stress lead to lobular inflammation, comprehensively resulting in fibrosis.

In the current study, the preventive effects of NTZ 100 mg/kg/day, ELA 1 mg/kg/day and the combination of both were assessed in a murine model. 6 week-old male C57Bl/6J mice were fed a control (CSAA) diet (n=8), CDAA+1% cholesterol diet (n=12), or CDAA+1% cholesterol diet supplemented with NTZ 100 mg/kg/day (n=8), ELA 1 mg/kg/day (n=8) or combined drugs (NTZ 100 mg/kg/day coadministered with ELA 1 mg/kg/day (n=8)) for 12 weeks. The food was purchased from Ssniff® company (Soest, Germany). Nitazoxanide (Interchim, Ref #RQ550), elafibranor (Genfit) or both compounds were incorporated by Ssniff® into CDAA+1% chol diet in powder form to the required dose.

The body weight and the food intake were monitored twice per week. On the last day of treatment, mice were sacrificed after a 6 h fasting period. The liver was rapidly excised for transcriptomic and histological studies.

All animal procedures were performed according to standard protocols and in accordance with the standard recommendations for the proper care and use of laboratory animals.

Transcriptomic Studies

RNA Extraction

Hepatic Total RNA was isolated using Nucleospin® 96 Kit (Macherey Nagel) following manufacturer's instructions. 150 ng of total RNA were reverse transcribed in cDNA using M-MLV-RT (Moloney Murine Leukemia Virus Reverse Transcriptase) (Invitrogen cat #28025) in presence of RT buffer 1× (Invitrogen cat #P/NY02321), 1 mM DTT (Invitrogen cat #P/NY00147), 0.5 mM dNTPs (Promega), 200 ng pdN6 (Roche cat #11034731001) and 40 U of Ribonuclease inhibitor (Promega cat #N2515).

RNA-Sequencing:

Upon measurement of RNA samples concentration by nanodrop, the quality was assessed using bioanalyser. Libraries were prepared using the Illumina TruSeq stranded mRNA LT kit and mRNA were sequenced using a NextSeq 500 device (paired-end sequence, 2×75 bp), with a High Output flow cell.

RNA-Seq Data Analysis:

Reads were cleaned using Trimmomatic v.0.36 with the following parameters: SLIDINGWINDOW: 5:20 LEADING: 30 TRAILING: 30 MINLEN: 60. Then reads were aligned on the genome reference (*Mus musculus* GRCm38.90) with rnacocktail using hisat2 v.2.1.0 as aligner with default parameters.

A count table was produced using featureCounts v1.5.3 with default parameters.

To identify differentially expressed genes (DE genes), we used R (version 3.4.3) and the DESEq2 library (v. 1.18.1). Gene annotations were retrieved using the AnnotationDbi library (v. 1.40.0). Briefly, the count matrix produced by FeatureCounts was analyzed by the DESeqDataSetFromMatrix( ) function followed by the DEseq( ) function from the DESeq2 library. For each condition (ie comparison NTZ+CDAA/c vs CDAA/c), the fold change and the p-value were retrieved using the results( ) function from DESeq2. The different tables were merged using the Ensembl ID as a key.

Histology

At sacrifice, liver samples were processed for histological analysis and examined as follows.

Tissue Embedding and Sectioning

The liver slices were first fixed for 40 hours in formalin 4% solution followed by several dehydration steps in ethanol (successive baths at 70, 80, 95 and 100% ethanol). The liver pieces were subsequently incubated in three xylene baths followed by two baths in liquid paraffin (58° C.). Liver pieces were then put into small racks that were gently filled with Histowax® to completely cover the tissue. Then, tissue samples were thicked in 3 μm sections. Sections were prepared for immunohistochemistry (IHC).

Immunohistochemistry Assay: 4-HNE (4-Hydroxynonenal):

Immunohistochemistry assay was performed by using an immunoperoxidase protocol. Sections were dewaxed at 58° C. and in xylene baths (2×3 min). The specimens were hydrated with ethanol (successive baths at 100%, 100%, 95% and 70%) (3 min each) and submerged in 1×PBS (2×5 min). Subsequently, endogenous peroxidase was blocked with H2O2 solution (0.3% H2O2 in distilled water) for 30 min, followed by three washes in 1×PBS for 5 min. Furthermore, heat mediated antigen retrieval was performed with citrate buffer at pH 6.0 for 40 min at 95° C. To block nonspecific binding, 1×PBS solution with 3% normal goat serum and 0.1% Triton was added for 60 min. Subsequently, the tissues were incubated with primary 4-HNE antibody overnight at 4° C. and rinsed with 1×PBS (3×5 min). The tissues were incubated with HRP secondary antibody for 1 h at room temperature and then rinsed with 1×PBS (3×5 min). Slides are then revelated with the peroxidase substrate 3,3'-diaminobenzidine ((DAB) for 15 min, and rinsed with tap water. Finally, the stains were counterstained with Mayer hematoxylin for 3 min and rinsed with tap water (2 min) and tissues were dehydrated in ethanol and xylene.

4-HNE IHC Analysis:

The histological examinations and scoring were performed blindly. Images were acquired using Pannoramic 250 Flash II digital slide scanner (3DHistech). Scoring: seven randomly selected fields from each section were examined and analyzed in QuantCenter software. 4-HNE accumulation was calculated as 4-HNE-positive area/total selected fields area.

ARE Reporter—HepG2 Cell Line

The ARE Reporter—Hep G2 cell line is designed to monitor Nrf2 antioxidant response pathway. The cell contains a firefly luciferase gene under the control of ARE (antioxidant response element) stably integrated into Hep G2 cells.

ARE reporter—HepG2 cells (BPS Bioscience, Inc., San Diego, cat #60513) were cultured following manufacturer's instructions. After thawing (BPS thaw medium 1K, cat #60187), cells were cultured in growth-medium (BPS growth medium 1K, cat #79533) and subsequently plated at a density of 40 000 cells per well in a 96-well microplate in 45 μL of assay medium (BPS thaw medium). TZ, ELA and DL-Sulforaphane (Sigma cat #S4441) were dissolved in DMSO and diluted into assay medium. 5 μl of dilution were added on cells to reach a final concentration of 1 μM for TZ and 3 μM for ELA. DL-Sulforaphane was used as a positive control at the dose of 3 μM. After 18 h exposure, luciferase activity was determined. 50 μL of One-Step Luciferase assay system (BPS cat #60690) were added per well and after ~15 min of rocking at room temperature, luminescence was measured using a luminometer.

Fold induction over DMSO above 2 and with a p-value $<0.05$ was considered as significant.

Statistical Analysis

Statistical analyses were performed using Prism Version 7, as follows:

In Vivo Studies

CSAA vs CDAA/c groups were compared by a Student t-test (#: $p<0.05$; ##: $p<0.01$; ###: $p<0.001$) or by a Mann-Whitney test ($: $p<0.05$; $$: $p<0.01$; $$$: $p<0.001$).

NTZ, ELA or ELA/NTZ treated group were compared to CDAA/c+1% chol diet using One-way ANOVA and uncorrected Fisher's LSD post-hoc (* $p<0.05$,  $p<0.01$, * $p<0.001$) or using Kruskal-Wallis test and uncorrected Dunn's test post-hoc. (§ $p<0.05$, §§ $p<0.01$, §§§ $p<0.001$).

In Vitro Studies

ARE Reporter Assay:

DMSO and DL-Sulforaphane (DLS) groups were compared by a Student t-test (#: $p<0.05$; ##: $p<0.01$; ###: $p<0.001$). Treated groups were compared with DMSO group as well as between them using One-way ANOVA and uncorrected Fisher's LSD post-hoc (* $p<0.05$,  $p<0.01$, * $p<0.001$).

Results 6 week-old C57BL/6 mice were fed a control (CSAA) diet, CDAA+1% CHOL (CDAA/c) diet, or CDAA/c diet supplemented with NTZ 100 mg/kg/day alone, ELA 1 mg/kg/day alone or combined NTZ 100 mg/kg/day/ELA 1 mg/kg/day for 12 weeks.

After the sacrifice, the hepatic levels of SOD1; SOD2, GPX, CAT, GSTA1, GTA2, GSTA4 transcripts were analyzed by RNAseq and the count levels were determined and data were normalized over the CDAA/c values. The results show that ELA and NTZ induced respectively a different subset of antioxidant genes in the liver that surprisingly led to a complementary signature when both drugs are combined.

Figure 2:
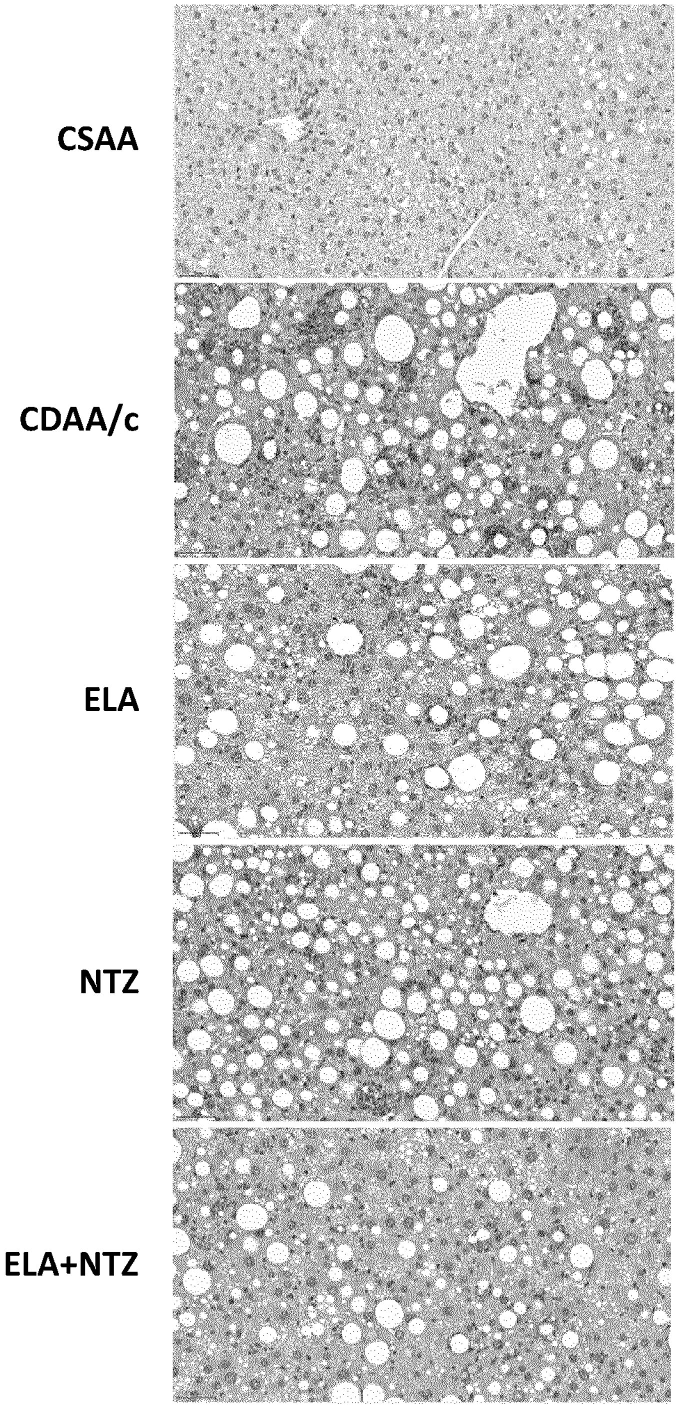
FIG. 2 shows representative images of 4-HNE staining for each mice group described in the legend of FIG. 1 (Magnification ×300).

4-HNE, a peroxidized aldehyde product of unsaturated fatty acids, is considered as a relevant indicator of oxidative stress (Takeuchi-Yorimoto, Noto et al. 2013). Our results show that an increase of intrahepatic 4-HNE levels is observed in the CDAA/c group in comparison with the CSAA group as shown in FIG. 1 and FIG. 2. Surprisingly, the levels of 4-HNE in the group that was exposed to the ELA/NTZ combination was reduced with an unexpected amplitude (−79%) in comparison with the CDAA/c group. Moreover, this therapeutic effect of the combination is higher than the effect obtained with each agent administered alone, showing an unexpected anti-oxidative stress effect of the combination of NTZ and ELA.

To further investigate the anti-oxidative stress effect of this combination, transcriptomic analyses were conducted on liver samples.

ELA (1 mg/kg/day) significantly induced the expression of a subset of antioxidant genes (SOD, Cat, GPX1) considered as the 1st line defense antioxidants meanwhile NTZ (100 mg/kg/day) significantly induced the expression of GST enzymes that are involved in detoxification of peroxidized products, a step that is downstream in the antioxidative signaling pathway. Interestingly, the results have shown that ELA/NTZ combination significantly induced the expression of several subsets of genes involved in different stages of the defense against oxidative stress, suggesting a more complete antioxidant defense mechanism when ELA and NTZ are co-administered in comparison with the result obtained with ELA or NTZ alone.

Figure 3:
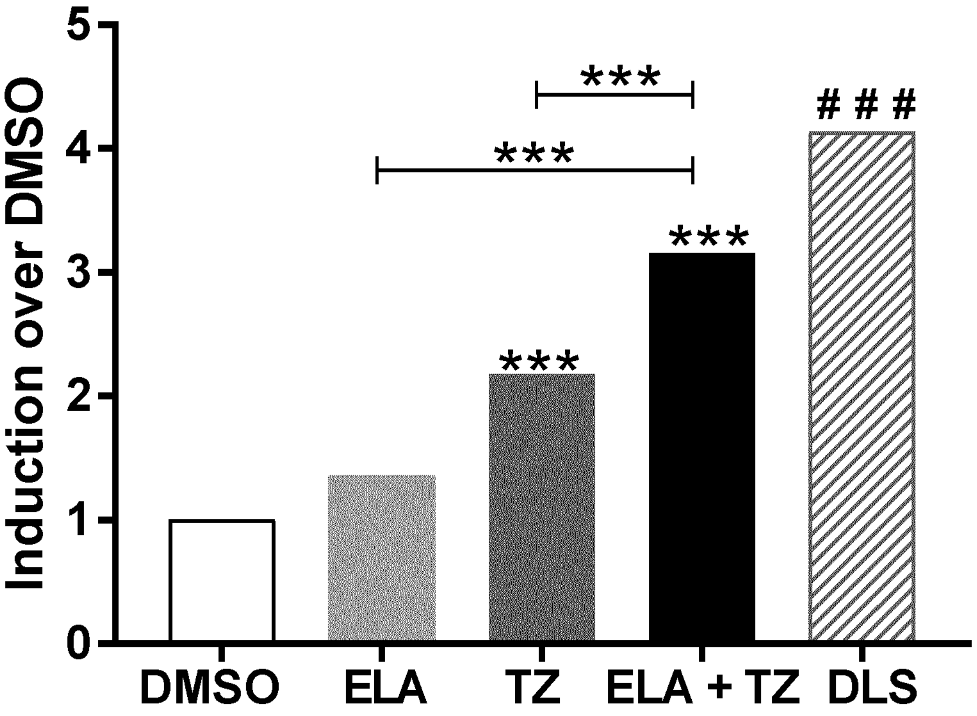
FIG. 3 shows the Nrf2-ARE-related transcriptional activity induced by TZ, ELA or the combination thereof. DL-Sulforaphane (DLS) was used as a positive control of induction. Data are shown as mean, ###: $p<0.001$, ***: $p<0.001$.

Since Nrf2 is a transcriptional master regulator of intracellular redox homeostatis (Hayes and Dinkova-Kostova 2014), we evaluated the effect of TZ (the active metabolite of NTZ), ELA and the combination thereof on the Nrf2-ARE-mediated transcription in human hepatocytes (FIG. 3). Unexpectedly, TZ, but not ELA, induces a significant activation of Nrf2-antioxidant pathway compared to the untreated condition and this induction is significantly higher with the combination compared to each agent alone demonstrating that a higher beneficial effect is obtained with the combination.

Altogether, these data suggest a stronger and more complete therapeutic response against oxidative stress when ELA/NTZ or ELA/TZ are combined together.

REFERENCES de Araújo, R., D. Martins, et al. (2016). "Oxidative Stress and Disease—from the edited volume: A Master Regulator of Oxidative Stress—The Transcription Factor Nrf2, Edited by Jose Antonio Morales-Gonzalez, Angel Morales-Gonzalez and Eduardo Osiris Madrigal-Santillan."

Hayes, J. D. and A. T. Dinkova-Kostova (2014). "The Nrf2 regulatory network provides an interface between redox and intermediary metabolism." Trends Biochem Sci 39 (4): 199-218.

Rossignol, J. F. and R. Cavier (1975). DE2438037A1—2-Benzamido-5-nitrothiazoles, S.P.R.L. Phavic, Belg. 11 pp.

Takeuchi-Yorimoto, A., T. Noto, et al. (2013). "Persistent fibrosis in the liver of choline-deficient and iron-supplemented L-amino acid-defined diet-induced nonalcoholic steatohepatitis rat due to continuing oxidative stress after choline supplementation." Toxicol Appl Pharmacol 268 (3): 264-277.

The invention claimed is:

1. A method of treating a disease involving oxidative stress comprising the administration, to a subject in need of treatment, a combination product comprising:

(i) elafibranor, 2-[2,6-dimethyl-4-[3-[4-(methylthio)phenyl]-3-oxo-propyl]phenoxy]-2-methylpropanoic acid, or a pharmaceutically acceptable salt of elafibranor or 2-[2,6-dimethyl-4-[3-[4-(methylthio)phenyl]-3-oxo-propyl]phenoxy]-2-methylpropanoic acid, and (ii) a compound selected from the group consisting of Nitazoxanide (NTZ), Tizoxanide (TZ), and a pharmaceutically acceptable salt of NTZ or TZ;

wherein the disease is selected from the group consisting of Alzheimer's disease, Parkinson's disease, Huntington's disease, tardive dyskinesia, epilepsy, acute diseases of the central nervous system, spinal cord injuries, brain trauma, ischemic brain damage, lung ischemia-reperfusion injury, stroke, and rheumatoid arthritis.

2. The method according to claim 1, wherein component (i) is elafibranor or a pharmaceutically acceptable salt thereof.

3. The method according to claim 1, wherein component (ii) is Nitazoxanide (NTZ), or a pharmaceutically acceptable salt of NTZ.

4. The method according to claim 1, wherein component (i) is elafibranor or a pharmaceutically acceptable salt thereof and component (ii) is NTZ or a pharmaceutically acceptable salt thereof.

5. The method according to claim 1, wherein said combination product is a pharmaceutical composition comprising component (i) and component (ii).

6. The method according to claim 1, wherein said combination product is a kit comprising:

a first pharmaceutical composition comprising component (i); and a second pharmaceutical composition comprising component (ii).

7. The method according to claim 1, wherein component (i) and component (ii) are formulated for oral administration.

8. The method according to claim 1, wherein component (i) and component (ii) are formulated in a pill, a tablet or a suspension for oral ingestion.

* * * * *